United States Patent [19]

Amin

[11] 4,414,968
[45] Nov. 15, 1983

[54] SURGICAL DRAPE

[76] Inventor: Shailesh R. Amin, 1417 Golf Ter., Danville, Ill. 61832

[21] Appl. No.: 268,367

[22] Filed: May 29, 1981

[51] Int. Cl.$^3$ .............................................. A61F 13/00
[52] U.S. Cl. ................................................ 128/132 D
[58] Field of Search .......... 128/132 D, 283, DIG. 24, 128/272

[56] References Cited

U.S. PATENT DOCUMENTS

| | | | |
|---|---|---|---|
| 2,759,477 | 8/1956 | Mains | 128/283 |
| 3,452,750 | 7/1969 | Blanford | 128/132 D |
| 3,650,267 | 3/1972 | Anderson | 128/132 D |
| 3,791,382 | 2/1974 | Collins | 128/132 D |
| 4,089,331 | 5/1978 | Hartigan et al. | 128/132 D |
| 4,169,472 | 10/1979 | Morris | 128/132 D |

Primary Examiner—C. Fred Rosenbaum
Assistant Examiner—T. J. Wallen
Attorney, Agent, or Firm—James W. Potthast

[57] ABSTRACT

A surgical drape for cystoscopic procedures having a fenestration for access to the site of the medical procedure and a foldable pocket located in the path of fluid runoff from the fenestration. A malleable frame holds the pocket open to receive the fluid runoff. The pocket has an upper portion with pleated side walls which assist in keeping the pocket open and a lower funnel-like portion ending in a drain hole. A coupler is provided for connection of the drain hole with an elongate house for conducting the fluid to a remote receptacle. A removable filter element is releasibly mounted between the upper portion of the pocket and the drain hole for filtering out solids from the fluid.

2 Claims, 5 Drawing Figures

SURGICAL DRAPE

SUMMARY OF THE INVENTION

One of the main objects of my invention is to provide an improved surgical drape for covering a patient's body during a surgical, or medical, procedure having a foldable pocket for collecting fluid runoff from the site of the surgical, or medical, procedure and having means for maintaining the pocket in an open position.

In a preferred embodiment of my invention, a surgical drape for a cystoscopic procedure has a sheet of drapable material with a fenestration adjacent an edge thereof. A foldable pocket is secured to the sheet at the other side of the edge to hang between and beneath the patient's legs in the path of fluid runoff. Adhesive strips on the underside of the sheet adjacent the fenestration secure the sheet to the patient's body to support the weight of the foldable pocket.

A pair of U-shaped malleable frame members are inserted into the pocket to maintain it in an open position. Relatively rigid pleats in the sidewalls of an upper portion of the pocket also function to keep the pocket open. A lower funnel portion of the pocket tapers down to a drain hole in the bottom of the pocket.

The other principal object of my invention is to provide an improved surgical drape having a foldable pocket for the collection of runoff fluids with a drain hole and means for coupling a hose with the drain hole for conduction of the collected fluid to a remote receptacle. In the preferred embodiment constructed in accordance with this objective, a male coupler is provided around the drain hole for insertion into the end of a hose. The lower portion of the pocket has a funnel-like shape to direct all the fluids to the drain hole.

A further feature of my invention is the provision of a surgical drape as summarized above in which a removable filter element is mounted inside the pocket between the opening and the drain hole for filtering out solid particles from the runoff fluid.

BRIEF DESCRIPTION OF THE DRAWINGS

Further objects, features and advantages will be made apparent and the foregoing objects, features and advantages will be described in greater detail in the following detailed description of my preferred embodiment which is given with reference to the several views of the drawing, in which.

DETAILED DESCRIPTION

Figure 1:
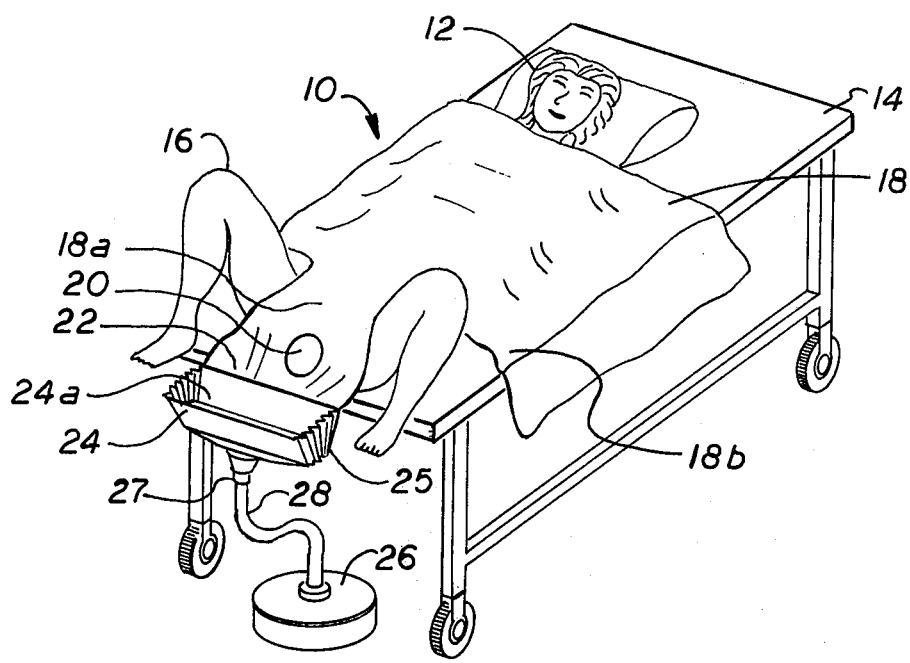
FIG. 1 is a perspective view of the preferred embodiment of my surgical drape as being used to cover a patient for a cystoscopic medical procedure.

Referring now to the drawings, particularly FIG. 1, the preferred embodiment of my surgical drape 10 is seen as being used to cover a patient 12 for surgical procedure on external genitalia, or perineum or for endoscopic urological procedures. The patient is shown lying on an office examination or surgical table 14, for my surgical drape is particularly useful whenever a standard urological table is not available. The legs 16 of the patient 12 are located at the edge of the table 14 and held by suitable means (not shown) in a raised position for the cystoscopic procedures.

The drape 10 comprises a sheet 18 made from suitable drapable material, such as cloth or paper. A fenestration 20 is located adjacent an edge 22 of a narrowed lower section 18a of sheet 18. Section 18a is narrowed relative to an upper section 18b to facilitate the fit between the legs 16 of patient 12.

Secured to sheet 18 at edge 22 is a foldable pocket 24. As seen in FIG. 1, pocket 24 hangs between and beneath the patient's legs 16 with its open top 24a in the path of fluid runoff 24 from the fenestration 20. The fluid from fenestration 20 comprises either bodily fluids released during the medical procedure or irrigation or anticeptic fluids used during the procedure. In either event it is the object of the invention to keep the fluids off the patient, the attending physician and the operating room floor by collecting the fluid in the foldable pocket 24.

The foldable pocket 24 is made of a suitable fluid impervious material and the fluid collected therein is conducted to a remote receptacle 26 by a flexible hose 28 connected to the bottom of pocket 24. The receptacle 26 may conveniently be located on the floor and beneath the table where it will not interfere with the movement of the attending physician during the procedure.

Advantageously, the receptacle 26 may be much larger than the pocket 24 and thus capable of holding much more fluid than pocket 24. In fact, since the hose 28 is disconnectable from the pocket 24, the same receptacle 26 may be successively used for multiple procedures on multiple patients. A shutoff valve or check valve 27 may be provided in hose 28 to prevent spillage due to backflow through the hose when disconnected from pocket 24.

Figure 2:
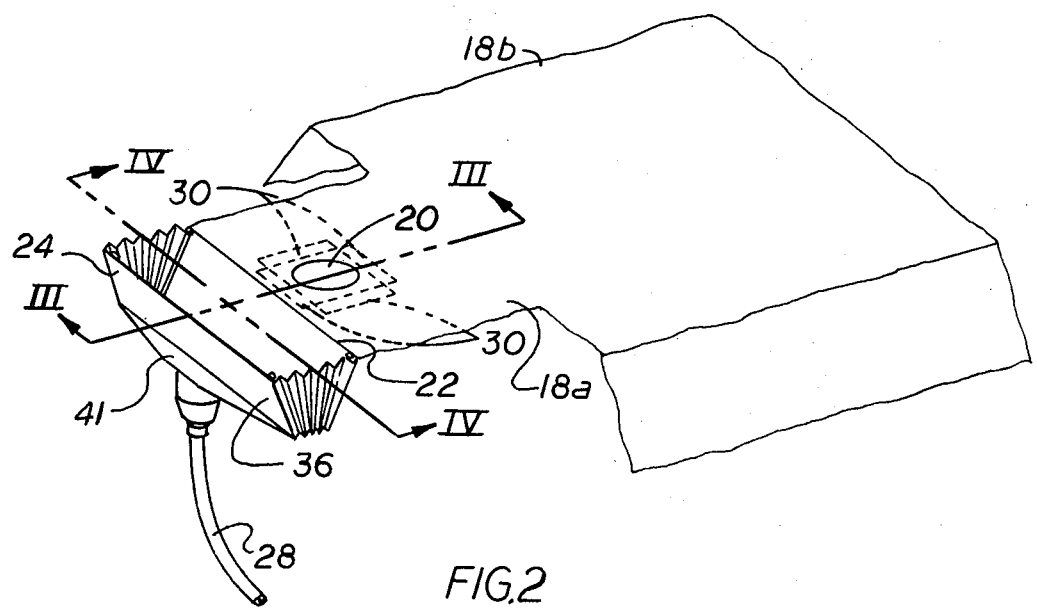
FIG. 2 is an enlarged perspective view of a portion of the surgical drape of FIG. 1.
Figure 5:
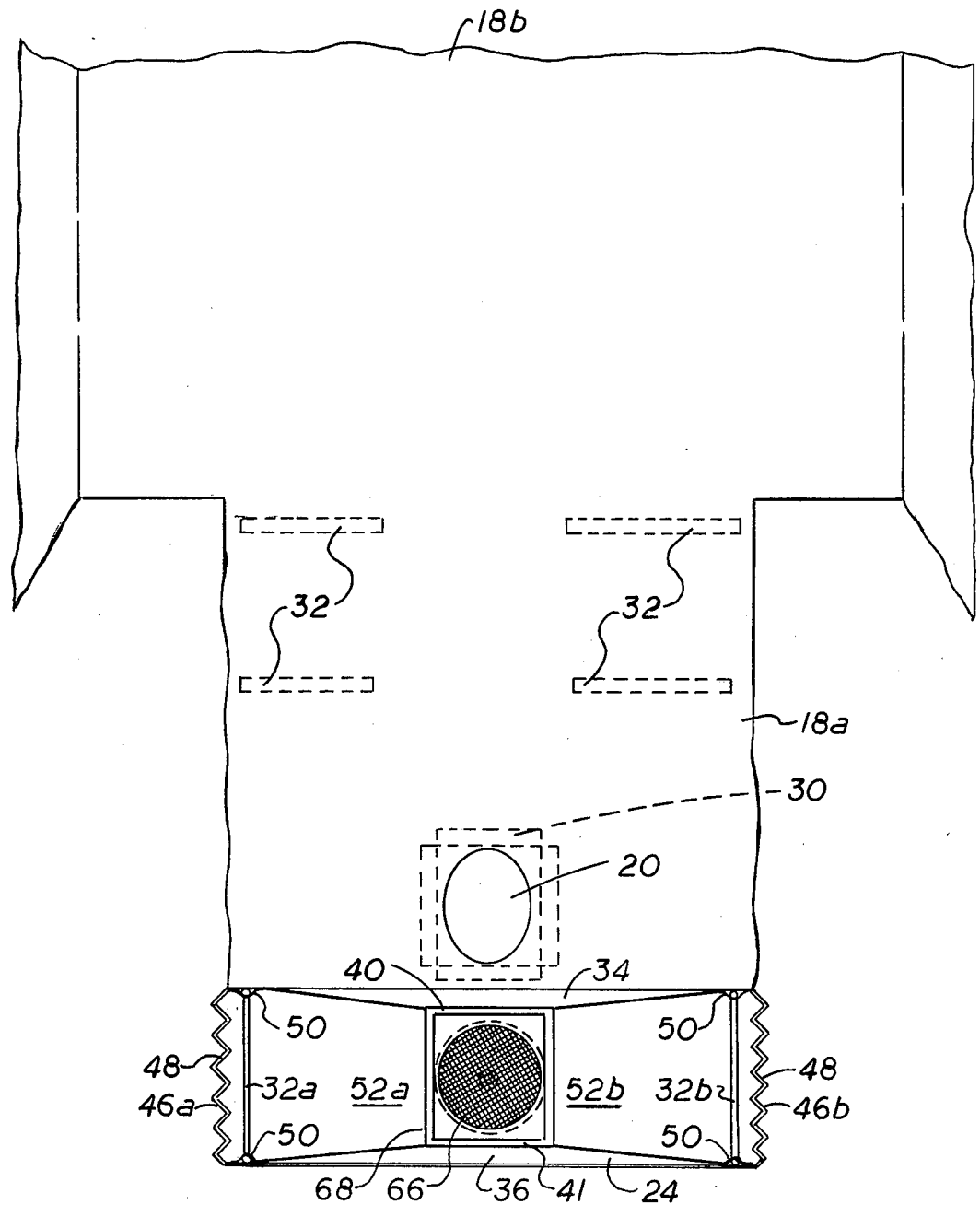
FIG. 5 is a plan view of the surgical drape of FIG. 2.

Referring now to FIGS. 2 and 5, adhesive strips 30 are mounted to the underside of lower section 18a adjacent fenestration 20. The adhesive strips 30 are provided to sufficiently secure the lower section 18a to the patient's body to support the weight of pocket 24 and hose 28 above the floor. Additionally, or alternatively, adhesive strips 32 spaced further from the fenestration may also be provided, as seen in FIG. 5. Preferably, the adhesive strips are covered with a suitable removable cover to prevent them from sticking until ready for use.

Figure 3:
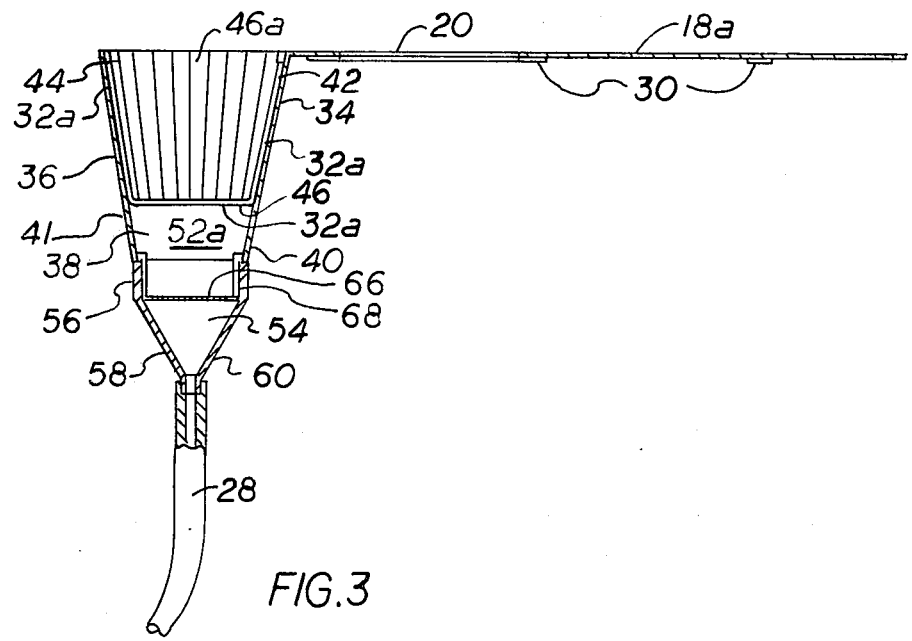
FIG. 3 is a sectional view of a portion of my surgical drape taken along section line III—III of FIG. 2.
Figure 4:
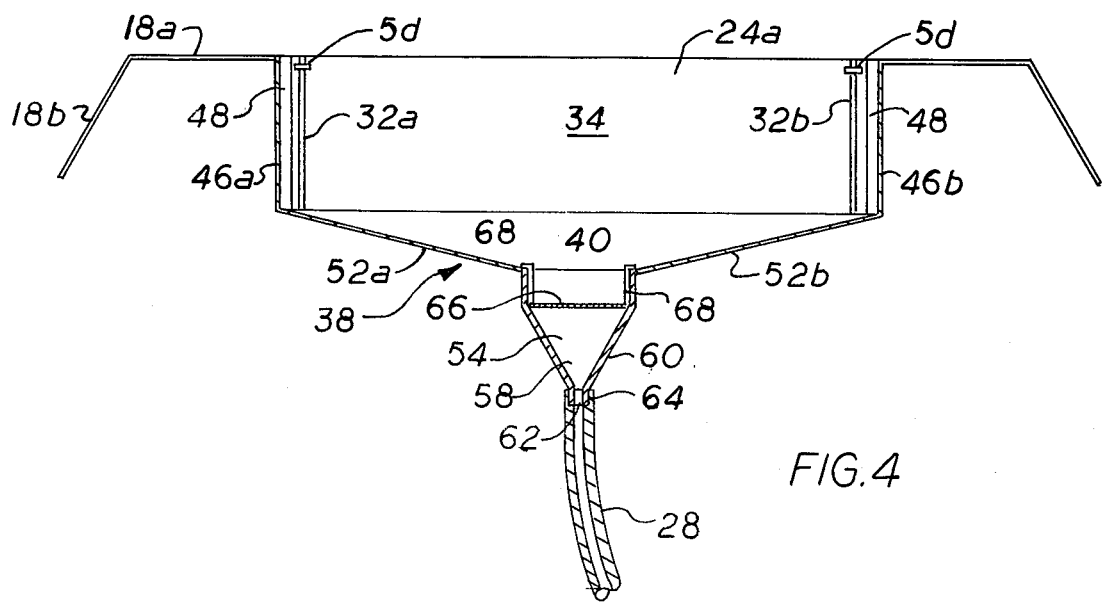
FIG. 4 is another section view of a portion of my drape taken along section line IV—IV of FIG. 2.

Referring now also to FIGS. 3 and 4, the pocket 24 is foldable for compact storage of the drape 10, and a pair of malleable, generally U-shaped frame members 32a and 32b are inserted in the pocket 24 during use to hold it open. The frame members 24 are substantially identical and are made from plastic, metal and other suitable malleable material which can be bent into different relatively rigid positions.

As best seen in FIG. 3, the pocket 24 has an upper portion with a back wall 34 and a front wall 36 which slope inwardly toward one another in a downward direction to a central portion 38 having slanted back and front walls 40 and 41 and slanted side walls 52a and 52b, FIG. 4. The frame members 32a and 32b are shaped to conform to this shape of the pocket 24. As seen in FIG. 3 with reference to frame member 32a, it has one leg 42 coextensive, parallel and adjacent to back wall 34. The opposite leg 44 is coextensive, parallel and adjacent to front wall 36. The cross leg 46 spans the gap between the front wall 36 and back wall 34 at central portion 38 and keeps the legs 42 and 44 in spaced relation.

Referring particularly to FIGS. 4 and 5, frame members 32a and 32b are located adjacent to and lie in a plane parallel to opposite side walls 46a and 46b. As best seen in FIG. 5, small constraining loops 50 are provided at the inside pocket 24 to hold the upper ends of frame member 32a and 32b in place next to the side walls 46a and 46b.

Preferably, side walls 46a and 46b have a series of substantially fan-fold pleats 48 to facilitate neat and compact folding of the pocket. Further, the pleats, when made of sufficiently stiff material, may also assist the frame members 32a and 32b in maintaining the pocket in an open position or solely perform this function in lieu of the frame members 32a and 32b. The frame members 32a and 32b may also be bent, so that the upward extending legs 42 and 44 will nestle within the pleats 48 adjacent the back wall 34 and front wall 36, so that loops 50 may be eliminated.

As best seen in FIG. 4, the slanted side walls 52a and 52b of central portion 38 extend downwardly from the bottom edge of the side walls 46a and 46b to the funnel 54. Slanted sidewalls 40 and 41 likewise terminate at funnel 54, as best seen in FIG. 4.

Funnel 54 has a rectangular cross section and comprises an upper filter-holding section 56 and a lower funnel section 58. The side walls 60 of funnel section 58 slope inwardly and downwardly to a drain hole 62. Surrounding drain hole 62 is a male coupler 64 for releasible connection with the flexable hose 28. Thus, the runoff fluids collected by pocket 24 are conducted down the sloping sides of the upper and middle portions of pocket 24, through funnel 54 and drain hole 62 to hose 28. As stated, hose 28 conducts the fluid to the remote receptacle 26.

A filter element 66 is fixedly mounted to a removable filter holder 68 which is releasibly seated in filter holding section 56 between the open top 24a and the drain hole 62. The filter element may be formed from metal on plastic mesh and functions to filter out solids from the runoff fluids collected by pocket 24. After the medical procedure, the filter holder 68 with its filter element 66 may be removed for examination, cleaned and, if desired, reused with a different drape.

While the funnel 54, as shown, is fixedly mounted to the opening at the bottom of slanted walls 52a and 52b, an alternate approach contemplated herein is to have the funnel 54 removably mounted to the drape so that it could be successively used with a plurality of such drapes. In such event, an apron is provided around the opening which is sealed to the outside of filter holding section 56 by means of a suitable circumferential fastener.

While a particular embodiment has been shown, it should be appreciated by those of ordinary skill in the art that many variations are possible without departing from the scope of my invention as defined in the claims.

I claim:

1. A drape for covering the body of a patient during a medical procedure, comprising:
   a sheet of drapable material having a fenestration for access to the site of the procedure;
   a foldable pocket carried by the sheet at a location in the path of fluid runoff from the fenestration and having a pair of opposite sides;
   a frame member insertable into the pocket for maintaining the foldable pocket in an open position to receive the fluid runoff; and
   means carried by said pocket for holding said frame member in an operable position adjacent either of said sides.

2. A drape for covering the body of a patient during a medical procedure, comprising:
   a sheet of drapable material having a fenestration for access to the site of the procedure;
   a foldable pocket carried by the sheet at a location in the path of fluid runoff from the fenestration and having a pair of opposite sides;
   means apart from the pocket itself for maintaining the foldable pocket in an open position to receive the fluid runoff including a frame member insertable into the pocket and means carried by said pocket for holding said frame member in an operable position adjacent either of said sides, said frame member being approximately U-shaped with an open portion at the top of the U, said open portion being located adjacent the pocket opening when the frame is inserted therein.

* * * * *